United States Patent
Emperaire

(10) Patent No.: US 7,235,524 B2
(45) Date of Patent: Jun. 26, 2007

(54) MEDICAMENTS FOR INITIATING OVULATION

(75) Inventor: Jean-Claude Emperaire, Bordeaux (FR)

(73) Assignee: Applied Research System ARS Holding N.V., Curacao (NL)

(*) Notice: Subject to any disclaimer, the term of this patent is extended or adjusted under 35 U.S.C. 154(b) by 241 days.

(21) Appl. No.: 10/140,819

(22) Filed: May 9, 2002

(65) Prior Publication Data

US 2002/0136774 A1 Sep. 26, 2002

Related U.S. Application Data

(62) Division of application No. 08/930,560, filed on Dec. 9, 1997, now Pat. No. 6,407,057.

(30) Foreign Application Priority Data

Jan. 31, 1997 (WO) .................. PCT/FR97/00198

(51) Int. Cl.
*A61K 38/24* (2006.01)
*A61K 9/00* (2006.01)

(52) U.S. Cl. .................. 514/2; 514/21; 530/313; 530/399; 424/400

(58) Field of Classification Search .................. 514/2, 514/21; 424/455, 457–459, 489–490, 497, 424/400; 530/313, 399
See application file for complete search history.

(56) References Cited

U.S. PATENT DOCUMENTS

| 4,767,628 A | * | 8/1988 | Hutchinson .................. 424/426 |
| 4,997,816 A | | 3/1991 | Hyland et al. |
| 5,304,377 A | | 4/1994 | Yamada et al. |
| 5,480,656 A | | 1/1996 | Okada et al. |

FOREIGN PATENT DOCUMENTS

| EP | EU 0 119 168 | 9/1984 |
| EP | 0 193 277 | 9/1986 |
| FR | 2 581 544 | 11/1986 |
| WO | WIPO 93/13799 | 7/1993 |

OTHER PUBLICATIONS

International Search Report for PCT/FR97/00198 dated Jun. 23, 1997.

* cited by examiner

*Primary Examiner*—Ruth A Davis
(74) *Attorney, Agent, or Firm*—Foley & Lardner LLP

(57) ABSTRACT

The invention relates to medicaments for initiating ovulation comprising LH in an administrable form which ensures an increase in LH plasma levels for a period of some 40 to 60 hours.

12 Claims, No Drawings

MEDICAMENTS FOR INITIATING OVULATION

This is a Divisional Application of application Ser. No. 08/930,560 filed Dec. 9, 1997 now U.S. Pat. No. 6,407,057.

The invention relates to medicaments for initiating ovulation.

It is known that ovulation is initiated physiologically by the release of LH, which takes place in the middle of the menstrual cycle and causes ovulation from ripe follicles; a release of FSH of smaller magnitude takes place simultaneously, probably acting synergistically with LH.

In treatment, it is preferable to provoke the initiation of ovulation for reasons of efficiency and programming even though spontaneous initiation of ovulation is always possible.

Chorionic gonadotropic hormone, or HCG, which is extracted from the urine of pregnant women and has biological activity of the LH type, has been very widely used for this purpose since the 1930s.

Since then the initiation of ovulation during menstrual cycles stimulated by anti-oestrogens or HMG has been brought about by a single injection of 5000 or 10000 I.U. of HCG.

HCG nevertheless has its own specificity with respect to LH, giving rise to reactions which differ according to the receptors, and which give it a prolonged half-life in comparison with LH.

HCG has the advantage of being effective in initiating ovulation and having a low production cost.

But it has very major potential disadvantages. Apart from the need to have sufficient collected urine to extract marketable quantities of HCG, two major risks may arise, namely an ovarian hyperstimulation effect, which might occur to a greater or lesser extent when HCG is administered with exaggerated follicular stimulation, and multiple pregnancies, which are a corollary of that complication. These two disadvantages significantly mar the use of HCG in treatment, and make it desirable to use LH for initiating ovulation.

The use of indigenous LH has been envisaged. With a few very rare exceptions, patients receiving ovulatory stimulation have a reserve of LH in the pituitary which can be mobilised through the use of GnRH itself, or one of its commercially available agonists. The administration of an agonist gives rise to a very major release of LH, which is wholly comparable with the pre-ovulatory physiological peak, but this release rarely lasts longer than 24 hours, whereas the physiological peak extends over about 48 hours.

This way of initiating ovulation with endogenous LH virtually eliminates the risk of ovarian hyperstimulation, as a result of the weaker biological activity of LH and its shorter half life in comparison with HCG. Its dilution half-life is in fact about 1 hour, and its elimination half life is about 24 hours, that is ten times shorter than that of HCG. Likewise it would seem that the risk of multiple pregnancies is smaller when this method is used.

Finally, the administration of a GnRH agonist also mobilises pituitary FSH synchronously with the release of LH, thus reproducing the physiological peak more faithfully.

However, the shortness of the period during which LH is released in this way is not appropriate for initiating ovulation in a number of women. Every woman has in fact a specific LH peak profile and in general an increase in LH for more than 24 hours is necessary to initiate ovulation under satisfactory conditions. It follows that the initiation of ovulation by endogenous LH mobilised by a GnRH agonist can depend on a luteal phase of satisfactory quality, with satisfactory chances for conception, but also, a short luteal phase (lasting 8 days or less) or an inadequate luteal phase (of normal length but with progesteronaemia below 8 ng/ml).

In order to overcome these disadvantages it has been suggested that exogenous LH obtained from the human pituitary should be used. However, for obvious reasons of availability, it has not been possible to continue experiments with such a material for a long time. Obtaining LH in recombinant form has made it possible to continue with this type of experimentation, but given the half life of LH the initiation of ovulation by recombinant LH means that large doses have to be injected. Smaller doses are likely to give rise to a relatively brief LH plasma peak in comparison with the physiological peak, and are likely to give rise to the same problems as with endogenous LH.

Injections then have to be repeated, which gives rise to the dual problem of acceptability by the patient and cost, as the production cost of recombinant LH is high.

The inventor's work in this field has demonstrated that the problems mentioned above can be overcome by administering LH in the form of a medicament which brings about a release which reproduces the physiological peak of approximately 48 hours more faithfully.

The invention therefore relates to the provision of new forms for the administration of medicaments based on LH for initiating ovulation.

Medicaments for the initiation of ovulation according to invention are characterised in that they incorporate LH in an administrable form which ensures an increase in the plasma level of LH for approximately 40 to 60 hours.

The use of LH in such an administrable form gives rise to a satisfactory ovulation process.

Advantageously the LH may be used in association with FSH, by which means the physiological process can be reproduced more faithfully and the quantity of LH required to initiate ovulation can undoubtedly be reduced.

Appropriate proportions correspond to a LH to FSH ratio of approximately 5.

Endogenous forms of these hormones or their $\alpha$ $\beta$ sub-units, or again recombinant forms of these hormones or their sub-units, such as are produced by genetic engineering, are used. It is also possible to use therapeutic analogues of LH or FSH, or peptide or non-peptide LH and FSH agonists, which may act over a long period. Compounds of this type may be produced by genetic engineering, or by synthesis, and are described for example by Boime et al., in "in GnRH, GnRH analogs, gonadotropins and gonadal peptides", P. Bouchard, A. Caraty, HJF Coeningh Bennink and SN Pavlov Eds, The Parthenon Publishing Group, London 1993, p. 347–356.

The administrable forms correspond to particles having a size of approximately 1 to 250$\mu$, see below.

In accordance with one embodiment of the invention these particles are based on a concentrate of LH and, if applicable, FSH.

Preferred particles of this type comprise lyophilisates, which may or may not be stabilised with sucrose and/or salts of dicarboxylic acids.

In accordance with another embodiment of the invention, the particles comprise a solid envelope enclosing the LH, which may be associated with FSH and pharmaceutical excipients.

The envelope may then control the release of the active ingredient.

Appropriate materials for forming the envelope comprise biodegradable polymers. Among these polymers mention may be made of polylactic acid or a copolymer of lactic acid and glycolic acid.

In accordance with other embodiments the particles comprise a continuous matrix of the supporting material within which the active ingredient is dispersed.

These different forms are administered by injection or as a subcutaneous or intramuscular implant.

The dose of LH injected to obtain satisfactory ovulation in this form should be between approximately 10,000 and 25,000 I.U.

Toxicological investigations performed show that the medicaments according to the invention are harmless.

Other features and advantages of the invention are provided in the examples which follow:

EXAMPLE 1

Injectable Preparation

Bottles containing microspheres of LH enclosing the following ingredients are prepared:
LH: 3 mg
Excipient: dl-lactic-coglycolic polymer: approximately 170 mg
Mannitol: 85 mg
Sodium carboxymethylcellulose: 30 mg
Polysorbate 80: 2 mg
The following are used as a suspension medium for one ampoule:
Mannitol: 16 mg
Water for injectable preparations: q.s.p. 2 g
The lactide-glycolide copolymer is a biocompatible and biodegradable synthetic polyester such as is used in human medicine, in particular for the manufacture of absorbable surgical sutures.

Preparation of the microspheres:
The procedure described by Ogawa et al. in Chem. Pharm. Bull., 36 (3) 1095–1103, 1988, is advantageously used.

The microspheres are obtained by transferring macromolecules in a solvated state to an interphase, namely the coacervate phase. The coacervation product is then transformed into a gel containing the particles of active ingredient, and then solidified.

A dispersion of the active ingredient in lactic-glycolic copolymer solution is then added slowly and with stirring. The solubility of the copolymer is progressively reduced by adding a non-solvent. The copolymer then coacervates slowly around the suspended LH particles. The microspheres are then hardened by immersion, separated by filtration, washed, dried and analysed to determine their LH content.

Suitable packaging is provided by adding other necessary ingredients for the preparation of an injection or a subcutaneous or intramuscular implant to the microspheres.

EXAMPLE 2

Toxicology Studies

No sign of toxicity appeared for doses up to 200,000 I.U./kg tested subcutaneously and intravenously, in either single dose acute toxicity tests or chronic toxicity tests. This dose represents at least 1000 times the dose which it is intended to use in clinical practice.

Acute toxicity measurements yielded an LD50 of the order of 100 mg in rats when administered intraperitoneally. The LD50 could not be determined at doses of 200,000 times the normal therapeutic dose (mice).

Chronic toxicity investigations in rats and monkeys at doses of 2, 20, 200 μg of microparticles/kg administered subcutaneously every day over a period of 6 months showed that the effects observed were essentially related to the activity of the LH, or the LH associated with FSH.

The invention claimed is:

1. A composition for initiating ovulation, comprising luteinizing hormone in a range of 10,000 to 25,000 I.U. in an administrable form, wherein administration of the composition reproduces the physiological peak of approximately 48 hours.

2. A composition according to claim 1, further comprising follicle stimulating hormone.

3. A composition according to claim 2, wherein at least one of the luteinizing hormone and the follicle stimulating hormone is selected from the group consisting of an endogenous hormone and its subunits, a recombinant hormone and its subunits, a hormone analogue, and a hormone agonist.

4. A composition according to claim 1, wherein the composition is in the form of particles of approximately 1 to 250μ.

5. A composition according to claim 4, wherein the particles are based on a concentrate of luteinizing hormone and, optionally, follicle stimulating hormone.

6. A composition according to claim 5, wherein the composition is stabilized using sucrose and/or salts of dicarboxylic acids.

7. A composition according to claim 4, wherein the particles comprise a solid envelope enclosing the luteinizing hormone, said luteinizing hormone optionally associated with follicle stimulating hormone and/or a pharmaceutical excipient.

8. A composition according to claim 7, wherein the envelope is prepared from biodegradable polymers.

9. A composition according to claim 8, wherein the biodegradable polymers are selected from the group consisting of polylactic acid, a copolymer of lactic acid, and glycolic acid.

10. A composition according to claim 8, wherein the particles comprise a continuous matrix of supporting material within which the luteinizing hormone, optionally associated with follicle stimulating hormone, is dispersed.

11. A composition according to claim 2, wherein the composition is in the form of particles of approximately 1 to 250μ.

12. A composition according to claim 3, wherein the composition is in the form of particles of approximately 1 to 250μ.

* * * * *